United States Patent [19]
Epperson et al.

[11] Patent Number: 5,948,817
[45] Date of Patent: Sep. 7, 1999

[54] POLYCYCLIC ETHYL ALKYLAMIDE MELATONERGIC AGENTS

[75] Inventors: James Epperson, Cromwell; Graham Johnson, Madison; Daniel J. Keavy, Killingworth; Katherine S. Takaki, Middletown, all of Conn.

[73] Assignee: Bristol-Myers Squibb Company, Princeton, N.J.

[21] Appl. No.: 09/034,912

[22] Filed: Mar. 4, 1998

Related U.S. Application Data

[60] Provisional application No. 60/039,885, Mar. 5, 1997.
[51] Int. Cl.$^6$ .......................... A61K 31/34; A61K 31/335; C07D 307/77; C07D 317/70
[52] U.S. Cl. .......................... 514/463; 514/450; 514/452; 514/453; 514/468; 549/348; 549/354; 549/358; 549/383; 549/432; 549/468
[58] Field of Search ..................................... 549/432, 468, 549/348, 354, 358, 383; 514/463, 468, 450, 452, 453

[56] References Cited

U.S. PATENT DOCUMENTS 5,736,578  4/1998  Watson et al. .......................... 514/630

FOREIGN PATENT DOCUMENTS

| 0 527 687 | 2/1993 | European Pat. Off. . |
| 0 747 345 | 12/1996 | European Pat. Off. . |
| WO 94/07487 | 4/1994 | WIPO . |
| WO 95/17405 | 6/1995 | WIPO . |
| WO 95/29173 | 11/1995 | WIPO . |

OTHER PUBLICATIONS

J. Arendt, et al., "Alleviation of jet lag by melatonin: preliminary results of controlled double blind trial", *British Med. J.*, 292, p. 1170, (May 3, 1986).

V. M. Cassone, et al., "Dose–Dependent Entrainment of Rat Circadian Rhythms by Daily Injection of Melatonin", *J. of Biological Rhythms*, 1 (3), pp. 219–229 (1986).

S. M. Reppert, et al., "Molecular characterization of a second melatonin receptor expressed in human retina and brain: The Mel$_{1b}$ melatonin receptor", *Proc. Natl. Acad. Sci., USA*, 92, pp. 8734–8738, (Sep. 1995).

S. M. Reppert, et al., "Cloning and Characterization of a Mammalian Melatonin Receptor that Mediates Reproductive and Circadian Responses", *Neuron*, 13, pp. 1177–1185, (Nov. 1994).

*Primary Examiner*—Evelyn Mei Huang
*Attorney, Agent, or Firm*—Aldo A. Algieri

[57] ABSTRACT

Novel polycyclic ethyl alkylamides of formula I are active as melatonergic agents.

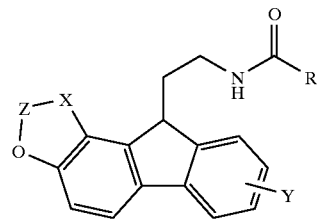

(I)

wherein

Z=CH (when a double bond is present) or $(CH_2)_n$, wherein n is 1–4;

X=O, $CH_2$, or CH (when a double bond is present);

R=$C_{1-6}$ alkyl, $C_{3-6}$ cycloalkyl, or $C_{1-3}$ haloalkyl, $C_{2-6}$ alkenyl, $C_{2-4}$ alkoxyalkyl, $C_{1-4}$ trifluoromethylalkyl, $C_{1-6}$ aminoalkyl; and Y=H, $C_{1-6}$ alkoxy or halogen.

13 Claims, No Drawings

POLYCYCLIC ETHYL ALKYLAMIDE MELATONERGIC AGENTS

CROSS REFERENCE TO RELATED APPLICATION

This nonprovisional application claims the benefit of copending provisional application U.S. Ser. No. 60/039,885 filed Mar. 5, 1997.

BACKGROUND

The invention pertains to novel polycyclic ethyl alkylamides having drug and bio-affecting properties and to their preparation, pharmaceutical formulations and use. In particular, the invention concerns fluorenes bearing substituted ethyl alkylamido or ethyl cycloalkyl amido groups. These compounds possess melatonergic properties that should make them useful in treating certain medical disorders.

Melatonin (N-acetyl-5-methoxytryptamine) is a hormone which is synthesized and secreted primarily by the pineal gland. Melatonin levels show a cyclical, circadian pattern with highest levels occurring during the dark period of a circadian light-dark cycle. Melatonin is involved in the transduction of photoperiodic information and appears to modulate a variety of neural and endocrine functions in vertebrates, including the regulation of reproduction, body weight and metabolism in photoperiodic mammals, the control of circadian rhythms and the modulation of retinal physiology.

Melatonin's structure is:

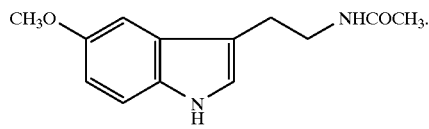

Recent evidence demonstrates that melatonin exerts its biological effects through specific receptors. Use of the biologically active, radiolabelled agonist [$^{125}$I]-2-iodomelatonin has led to the identification of high affinity melatonin receptors in the CNS of a variety of species. The sequences of two cloned human melatonin receptors have been reported [Reppert, et al., *Proc. Natl. Acad. Sci.* 92: 8734–8738, (1995) and Reppert, et al., *Neuron* 13: 1177–1185, (1994)]. In mammalian brain, autoradiographic studies have localized the distribution of melatonin receptors to a few specific structures. Although there are significant differences in melatonin receptor distribution even between closely related species, in general the highest binding site density occurs in discreet nuclei of the hypothalamus. In humans, specific [$^{125}$I]-2-iodomelatonin binding within the hypothalamus is completely localized to the suprachiasmatic nucleus, strongly suggesting the melatonin receptors are located within the human biological clock.

Exogenous melatonin administration has been found to synchronize circadian rhythms in rats (Cassone, et al., *J. Biol. Rhythms*, 1:219–229, 1986). In humans, administration of melatonin has been used to treat jet-lag related sleep disturbances, considered to be caused by desynchronization of circadian rhythms (Arendt, et al., *Br. Med. J.* 292:1170, 1986). Further, the use of a single dose of melatonin to induce sleep in humans has been claimed by Wurtman in International Patent Application WO 94/07487.

Thus, melatonin agonists should be particularly useful for the treatment of sleep disorders and other chronobiological disorders. Melatonin agonists would also be useful for the further study of melatonin receptor interactions as well as in the treatment of conditions affected by melatonin activity, such as depression, jet-lag, work-shift syndrome, sleep disorders, glaucoma, reproduction, cancer, premenstrual syndrome, immune disorders, inflammatory articular diseases and neuroendocrine disorders.

The compounds of this invention are melatonin agonists. However, they do not have the side effects associated with some melatonin agonists.

Aside from simple indole derivatives of melatonin itself, various bicyclic structures have been prepared and their use as melatonin ligands disclosed. In general these bicyclic amide structures can be represented as:

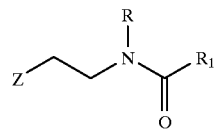

wherein Z is an aryl or heteroaryl system attached by a two carbon bridge to the amide group. Some specific examples follow.

Yous, et al. in European Patent Application EPA 527 687A disclose as melatonin ligands arylethylamines 1,

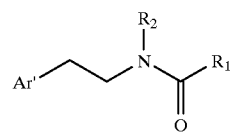

wherein Ar' is, inter alia, a substituted or unsubstituted benzo[b]thiophen-3-yl, benzimidazol-1-yl, benzo[b]furan-3-yl, 1,2-benzisoxazol-3-yl, 1,2-benzisothiazol-3-yl, or indazol-3-yl radical; $R_1$ is, inter alia, an alkyl or cycloalkyl group; and $R_2$ is hydrogen or lower alkyl.

North et al., in WO 95/29173, published Nov. 2, 1995, discuss naphthalene derivatives of structure 2:

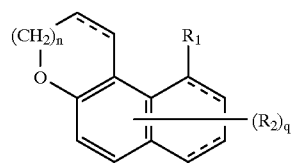

wherein $R_1$ is a group of the formula $CR_3R_4(CH_2)_p NR_5COR_6$; $R_2$ is hydrogen, halogen, $C_{1-6}$ alkyl, $OR_7$ or $CO_2R_7$; and may be the same or different substituent when q is 2; $R_3$, $R_4$ and $R_5$, which may be the same or different, are hydrogen or $C_{1-6}$ alkyl; $R_6$ is $C_{1-6}$ alkyl or $C_{3-7}$ cycloalkyl; $R_7$ is hydrogen or $C_{1-6}$ alkyl; n is zero, 1 or 2; p is an integer of 1, 2, 3 or 4; q is 1 or 2; and the dotted lines indicate the absence or presence of an additional bond. These compounds are taught to treat chronobiological disorders.

In WO 95/17405, North et al., disclose compounds of structure 3 and teach their use in the treatment of conditions related to the melatonin system. Structure 3 is:

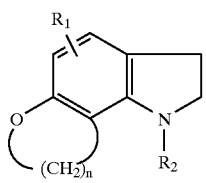

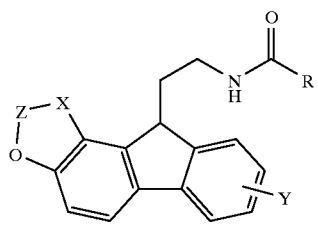

wherein $R_1$ is hydrogen, halogen or $C_{1-6}$ alkyl; $R_2$ is a group of formula $-CR_3R_4(CH_2)_pNR_5COR_6$; $R_3$, $R_4$ and $R_5$, which may be the same or different, are hydrogen or $C_{1-6}$ alkyl; $R_6$ is $C_{1-6}$ alkyl or $C_{3-7}$ cycloalkyl; n is an integer of 2, 3 or 4; and p is an integer of 1, 2, 3 or 4.

European Patent Application EP 0 747 345 A2 discloses ethylamido-fluorenes of structure 4 and improved methods of making same. Structure 4 is:

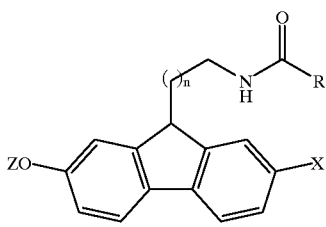

wherein:

X=H, halogen, OH or OZ;

Z=$C_{1-6}$ alkyl; $-(CH_2)_m-CF_3$ (m=0–2); $CD_3$; or

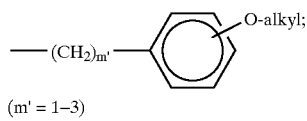

(m' = 1–3)

n=1 or 2; and

R=$C_{1-6}$ alkyl, $C_{3-6}$ cycloalkyl, $C_{2-4}$ alkenyl, halogen substituted $C_{1-6}$ alkyl, or $C_{1-6}$ alkoxy substituted $C_{1-6}$ alkyl.

The foregoing disclosures do not teach or suggest the novel melatonergic benzodioxole or dihydrobenzofurans of the present invention. The novel compounds of the present invention display melatonergic agonist activity which would not have been predicted based upon available literature.

SUMMARY AND DETAILED DESCRIPTION OF THE INVENTION

The invention involves a novel series of compounds of Formula I and solvates thereof. Formula I is:

wherein

Z=CH (when a double bond is present) or $(CH_2)_n$, wherein n is 1–4;

X=O, $CH_2$, or CH (when a double bond is present);

R=$C_{1-6}$ alkyl, $C_{3-6}$ cycloalkyl, or $C_{1-3}$ haloalkyl, $C_{2-6}$ alkenyl, $C_{2-4}$ alkoxyalkyl, $C_{1-4}$ trifluoromethylalkyl, $C_{1-6}$ aminoalkyl; and Y=H, $C_{1-6}$ alkoxy or halogen.

Z may be CH (when a double bond is present) or $(CH_2)_n$. Compounds in which Z is $CH_2$ are preferred. That is, compounds in which n is 1 are preferred.

X may be O, $CH_2$ or CH (when a double bond is present). Compounds in which X is $CH_2$ are preferred.

R is selected from $C_{1-6}$ alkyl, $C_{3-6}$ cycloalkyl and $C_{1-6}$ aminoalkyl groups. Compounds in which R is ethyl or cyclopropyl are preferred.

Y is selected from H, $C_{1-6}$ alkoxy and halogen. It is preferred that Y be H or methoxy.

"Alkyl" means a monovalent straight or branched chain group of the formula $C_xH_{2x+1}$, with x being the number of carbon atoms.

"Cycloalkyl" groups are monovalent cyclic moieties containing at least 3 carbon atoms and conforming to the formula $C_xH_{(2x-1)}$, with x being the number of carbon atoms present. The cyclopropyl group is a preferred cycloalkyl moiety.

"Alkylamino" refers to $-NH$-alkyl substituents containing 1 to 6 carbon atoms, preferably $-NHCH_3$ or $-NHCH_2CH_3$ groups.

"Alkoxy" designates alkyloxy, or alkyl-O-groups containing the stated number of carbon atoms.

"Halogen" refers to chlorine, bromine, iodine or fluorine with fluorine preferred.

Preferred compounds have $IC_{50}$ values of 250 nM or less in melatonergic binding tests described herein.

One group of preferred compounds include those of Formula I in which X is $CH_2$, Y is H, Z is $CH_2$ and R is $C_{1-6}$ alkyl.

This group includes:

N-[2-(2,10-dihydro-1H-fluoreno[2,1-b]furan-10-yl)ethyl] propanamide.

Another group of preferred compounds include those of Formula I wherein X is O, Y is $OCH_3$, Z is $CH_2$ and R is $C_{1-6}$ alkyl.

This group includes:

N-[2-(8-Methoxy-10H-fluoreno[1,2-d]-1,3-dioxol-10-yl) ethyl]propanamide.

Additionally, compounds of Formula I encompass all solvates, particularly hydrates, thereof. The present invention also encompasses stereoisomers as well as optical isomers, e.g. mixtures of enantiomers as well as individual enantiomers and diastereomers, which arise as a consequence of structural asymmetry in certain compounds of Formula I. Separation of the individual isomers is accomplished by application of various methods which are well known to practitioners in the art.

Compounds of Formula I can be prepared using the overall processes shown in the following schemes:

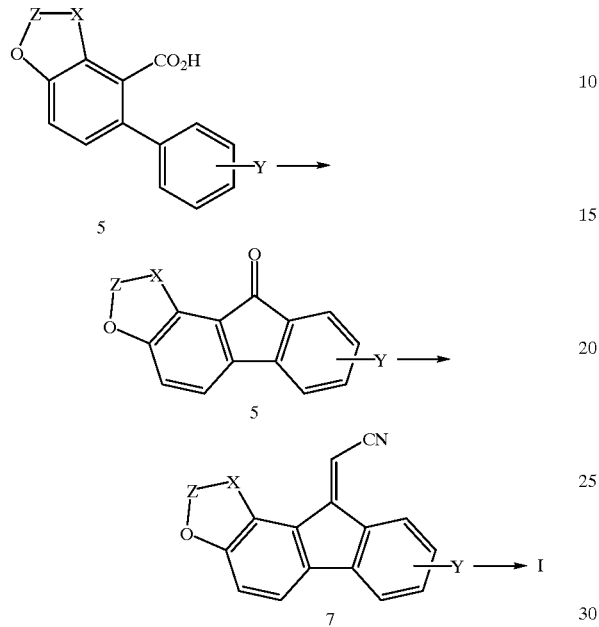

Intramolecular cyclization of an appropriately substituted biphenyl carboxylic acid 5 to the fluorenone derivative 6 can be accomplished directly by heating 5 in polyphosphoric acid or refluxing thionyl chloride. Alternatively, 5 can be converted to the acid chloride using reagents such as thionyl chloride, phosphoryl chloride or the like and the acid chloride can subsequently be cyclized to 6 by treatment with a strong Lewis acid such as aluminum chloride. 6 can be converted to the unsaturated nitrile derivative 7 by treatment with reagents such as diethyl cyanomethyl-phosphonate and a strong base such as sodium hydride or sodium ethoxide. 7 can be reduced to the saturated amine by catalytic hydrogenation and then treated with acylating reagents to give compounds of Formula I. Suitable acylating agents include carboxylic acid halides, anhydrides, acyl imidazoles, alkyl isocyanates, and carboxylic acids in the presence of condensing agents such as carbonyl imidazole, carbodiimides, and the like. Alternatively, Z can be converted directly to compounds of Formula I by catalytic hydrogenation in the presence of the appropriate anhydride.

When $X=CH_2$ and $Z=(CH_2)_n$ the intermediate biphenyl carboxylic acid 5 can be prepared as shown in Scheme 2.

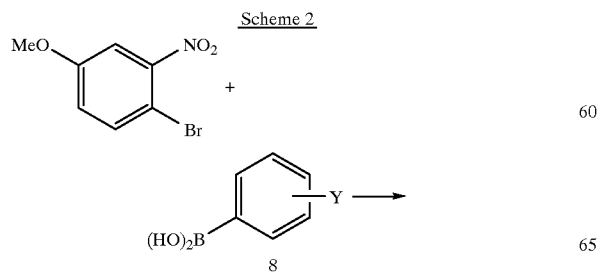

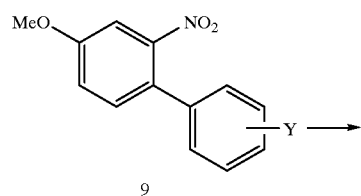

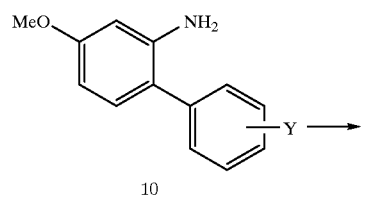

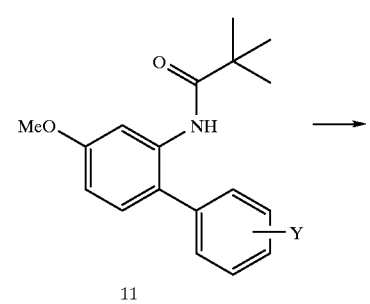

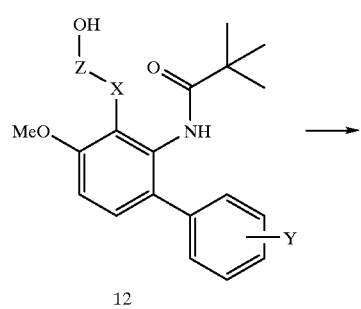

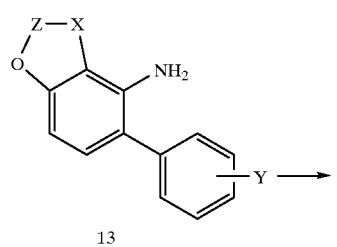

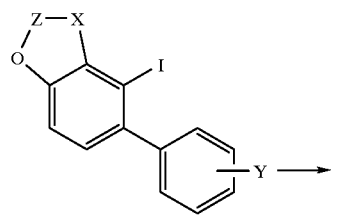

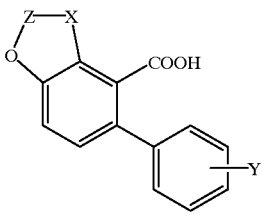

5

X = CH₂
Z = (CH2)ₙ

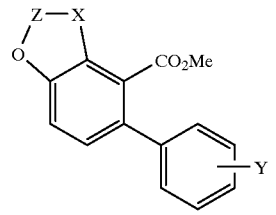 

17

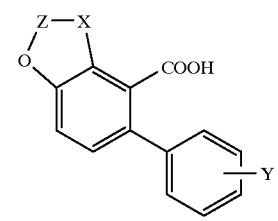

5

X = O
Z = (CH2)ₙ

Coupling of 4-bromo-3-nitroanisole with an appropriately substituted phenylboronic acid can be accomplished using a palladium catalyst such as tris(dibenzylideneacetone) dipalladium(0) or palladium(II) acetate and a base such as sodium carbonate, sodium hydroxide, potassium fluoride, or potassium phosphate in solvents such as DME, benzene, THF or acetone. The resulting nitrobiphenyl 9 can be reduced by catalytic hydrogenation to the biphenyl amine 10 which can then be acylated by treatment with pivaloyl chloride in the presence of a base such as pyridine, triethylamine or potassium carbonate to give the intermediate 11. 11 can be converted to 12 by treatment with a strong base such as n-butyl- or tert-butyllithium and trapping of the resulting anion with an appropriate electrophile such as ethylene oxide. 12 can be converted to the benzofuranyl amine 13 by heating in the presence of a strong acid such as HBr or sulfuric acid. 13 can then be converted to the iodide 14 by formation of the diazonium salt and treatment with potassium iodide. The biphenyl carboxylic acid 5 in which X=CH₂ and Z=(CH₂)ₙ can then be formed from 14 by treatment with tert-butyllithium followed by anhydrous carbon dioxide.

When X=O and Z=(CH₂)ₙ the intermediate biphenyl carboxylic acid 5 can be prepared as shown in Scheme 3.

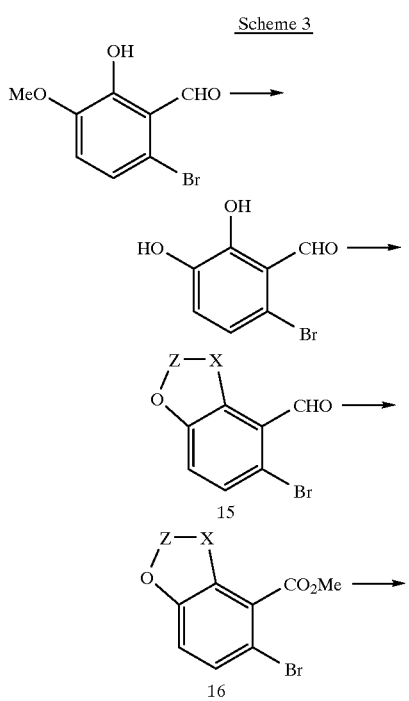

6-Bromo-2-hydroxy-3-methoxybenzaldehyde can be demethylated using standard deprotection methods such as treatment with boron tribromide, boron triiodide or boron trichloride in halogenated solvents such as methylene chloride and dichloroethane or heating with lithium chloride or lithium iodide in solvents such as collidine or DMF. The resulting 6-bromo-2,3-dihydroxybenzaldehyde can be converted to the cyclic derivative 15 by treatment with a suitable dihaloalkyl compound such as dibromomethane or dibromoethane and either potassium fluoride or cesium fluoride in DMF with heat or sodium hydroxide and a phase transfer catalyst in water. 15 can be converted to 16 by treatment with oxidants such as potassium permanganate or silver oxide followed by esterfication using standard conditions. Coupling of 16 with an appropriately substituted phenylboronic acid can be accomplished using a palladium catalyst such as tris(dibenzylideneacetone)dipalladium(0) or palladium(II) acetate and a base such as sodium carbonate, sodium hydroxide, potassium fluoride, or potassium phosphate in solvents such as DME, benzene, THF or acetone. The biphenyl carboxylic acid 5 in which X=O and Z=(CH₂)ₙ can then be formed from 17 by hydrolysis under standard conditions.

The Compounds

The compounds of the invention are melatonergic agents. They have been found to bind human melatonergic receptors expressed in a stable cell line with good affinity. Further, the compounds are agonists as determined by their ability, like melatonin, to block the forskolin-stimulated accumulation of cAMP in certain cells. Due to these properties, the compounds and compositions of the invention should be useful as sedatives, chronobiotic agents, anxiolytics, antipsychotics, analgesics, and the like. Specifically, these agents should find use in the treatment of stress, sleep disorders, seasonal depression, appetite regulation, shifts in circadian cycles, melancholia, jet-lag, glaucoma, reproductive disorders, cancer, premenstrual syndrome, immune disorders, inflammatory diseases, neuroendocrine disorders and related conditions.

The compounds of the invention are superior to melatonin in that they possess reduced vasoconstrictive properties.

In making pharmaceutical compositions containing compounds of the present invention, the active ingredient(s) will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form, each dosage containing from about 0.1 to 500 mg, more usually 1 to 100 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

These active compounds are effective over a wide dosage range. For example, dosages per day will normally fall within the range of about 0.1 to 500 mg. In the treatment of adult humans, the range of about 0.1 to 100 mg/day, in single or divided doses, is preferred. Generally, the compounds of the invention may be used in treating sleep and related disorders in a manner similar to that used for melatonin.

However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms.

DESCRIPTION OF SPECIFIC EMBODIMENTS

The compounds which constitute this invention, their methods of preparation and their biologic actions will appear more fully from consideration of the following examples, which are given for the purpose of illustration only and are not to be construed as limiting the invention in sphere or scope. In the following examples, used to illustrate the foregoing synthetic processes, temperatures are expressed in degrees Celsius and melting points are uncorrected. The nuclear magnetic resonances (NMR) are spectral characteristics refer to chemical shifts ($\delta$) expressed as parts per million (ppm) versus tetramethylsilane (TMS) as reference standard. The relative area reported for the various shifts in the $^1$H NMR spectral data corresponds to the number of hydrogen atoms of a particular functional type in the molecule. The nature of the shifts as to multiplicity is reported as a broad singlet (bs), singlet (s), multiplet (m), doublet (d), or triplet (t). Abbreviations employed are DMSO-$d_6$ (deuterodimethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed using the compound neat as a film or by employing potassium bromide (KBr) as diluent. The elemental analyses are reported as percent by weight.

Preparation

Preparation of intermediates of formula 5 where X=CH$_2$ and Z=(CH$_2$)$_n$.

Step 1

4-Methoxy-2-nitro-1,1'-biphenyl: A magnetically stirred suspension of 4-bromo-3-nitroanisole (64.41 g, 278 mmol), phenylboronic acid (36.15 g, 296 mmol), and tris(dibenzylideneacetone)dipalladium(0) in dimethoxyethane (375 mL)/2 N sodium carbonate solution (517 mL) was stirred for 3 d under nitrogen. Additional tris(dibenzylideneacetone)-dipalladium(0) (0.5 g) was added and the suspension was stirred for 12 h, treated with Et$_2$O (200 mL) and brine (200 mL), and the layers were separated. The aqueous layer was further extracted with fresh Et$_2$O (2×300 mL), the combined organic extracts were filtered through Celite with diethyl ether elution, washed with water (500 mL) and brine (500 mL), dried (K$_2$CO$_3$), filtered, and concentrated in vacuo to afford 27.89 g (44%) of the title compound: $^1$H NMR (300 MHz, CDCl$_3$) $\delta$ 3.88 (s, 3H), 7.12 (dd, J=8, 2 Hz, 1H), 7.23–7.29 (m, 2H), 7.32–7.42 (m, 5H).

Step 2

4-Methoxy-[1,1'-biphenyl]-2-amine: A Parr bottle charged with 4-methoxy-2-nitrobiphenyl (27.6 g, 120 mmol), Raney nickel (1.5 g), ethanol (100 mL), and H$_2$O (100 mL) was rocked under hydrogen (60 psi) for 3 h. The suspension was filtered through Celite, the cake washed with ethanol (500 mL) and tetrahydrofuran (500 mL), and the filtrate concentrated in vacuo. The residual suspension was digested with CH$_2$Cl$_2$ (300 mL), washed with H$_2$O (300 mL), and the organic portion extracted with 1 N HCl (4×200 mL). The combined extracts were made basic with 50% NaOH, extracted with CH$_2$Cl$_2$ (3×200 mL), and the organic extracts washed with brine (300 mL), dried (K$_2$CO$_3$), filtered, and concentrated in vacuo to give 24 g (100%) of the title compound which was used without further purification: $^1$H NMR (300 MHz, CDCl$_3$) $\delta$ 3.78 (s, 3H), 3.90 (br s, 2H), 6.34 (d, J=2 Hz, 1H), 6.41 (dd, J=8, 2 Hz, 1H), 7.03 (d, J=8 Hz, 1H), 7.15–7.33 (m, 2H), 7.36–7.41 (m, 3H).

Step 3

N-(4-Methoxy-[1,1'-biphenyl]-2-yl)-2,2-dimethylpropanamide: A magnetically stirred solution of 4-methoxybiphenyl-2-ylamine (25.27 g, 127 mmol) in CH$_2$Cl$_2$ (300 mL)/pyridine (300 mL) at 0° C. under nitrogen was treated with pivaloyl chloride via syringe (16.8 g, 17.2 mL, 139 mmol). The resultant suspension was stirred for 12 h at room temperature and concentrated in vacuo. The residue was digested with CH$_2$Cl$_2$ (300 mL), washed with 1 N HCl (2×300 mL), 1 N NaOH (2×300 mL), H$_2$O (300 mL), brine (300 mL), dried (K$_2$CO$_3$), filtered, and concentrated in vacuo to give 33.6 g (93%) of a white solid: $^1$H NMR (300 MHz, CDCl$_3$) $\delta$ 1.07 (s, 9H), 3.83 (s, 3H), 6.69 (dd, J=8.5, 2 Hz, 1H), 7.12 (d, J=8.5 Hz, 1H), 7.29–7.47 (m, 5H), 7.53 (br s, 1H), 8.13 (d, J=2 Hz, 1H).

Step 4

N-[3-(2-Hydroxyethyl)-4-methoxy-[1,1'-biphenyl]-2-yl]-2,2-dimethylpropanamide: A mechanically stirred solution of N-(4-methoxybiphenyl-2-yl)-2,2-dimethylpropionamide (17.91 g, 63.2 mmol) in anhydrous THF at −68° C. was treated dropwise with butyllithium (2.46 M in hexane, 72.0 mL, 177 mmol), stirred 1 h, allowed to warm to −5° C., stirred 1 h, cooled to −78° C., and treated with ethylene oxide (10.0 mL, 8.82 g, 200 mmol) in one portion. The suspension was allowed to warm to room temperature and stirred for 12 h. The suspension was treated with water (50 mL) and glacial acetic acid (2 mL), stirred 10 min, and concentrated in vacuo. The residue was treated with water (500 mL) and $Et_2O$ (300 mL), and the layers were separated. The aqueous layer was further extracted with diethyl ether (2×300 mL), the combined organic extracts were washed with saturated sodium bicarbonate (500 mL), brine (500 mL), dried ($K_2CO_3$), filtered, and concentrated in vacuo to give a solid. Recrystallization from $Et_2O$/hexanes gave 10.85 g (52%, 2 crops) of the compound as white crystals: $^1H$ NMR (300 MHz, $CDCl_3$) δ 1.04 (s, 9H), 2.00 (br s, 1H), 2.89 (t, J=6 Hz, 2H), 3.85 (s, 3H), 3.91 (t, J=6 Hz, 2H), 6.88 (d, J=8 Hz, 1H), 7.18 (d, J=8 Hz, 1H), 7.26–7.36 (m, 5H), 7.50 (br s, 1H).

Step 5

2,3-dihydro-5-phenyl-4-benzofuranamine: A pressure bottle was charged with N-[3-(2-hydroxyethyl)-4-methoxy-[1,1'-biphenyl]-2-yl]-2,2-dimethylpropanamide (10.77 g, 32.9 mmol), 48% HBr solution (200 mL), flushed with nitrogen, capped, and stirred at 95° C. for 12 h. The suspension was cooled to room temperature and poured over 200 g of ice/water. The aqueous phase was washed with $Et_2O$ (2×100 mL) and concentrated in vacuo to give a tan solid. The solid was redigested with $H_2O$ (200 mL), concentrated in vacuo, and dried (0.5 mm, 18 h). The resultant solid was digested with 1 N NaOH (300 mL), the resultant suspension extracted with $CH_2Cl_2$ (3×300 mL), and the combined extracts dried ($K_2CO_3$), filtered, and concentrated in vacuo to give the free amine (2.01 g, 21%) as an oil. $^1H$ NMR (300 MHz, $CDCl_3$) δ 3.05 (t, J=8.5 Hz, 2H), 4.64 (t, J=8.5 Hz, 2H), 6.34 (d, J=8 Hz, 1H), 6,91 (d, J=8 Hz, 1H), 7.29–7.45 (m, 7H).

Step 6

2,3-Dihydro-4-iodo-5-phenylbenzofuran: A mechanically stirred solution of 2,3-dihydro-5-phenyl-4-benzofuranamine (1.88 g, 8.90 mmol), ice (~5 g), and concentrated hydrochloric acid (3.9 mL) at 5° C. was treated slowly with a solution of sodium nitrite (0.675 g, 9.78 mmol) in $H_2O$ (4 mL). The resulting suspension was stirred 15 min and filtered through a plug of glass wool into a solution of potassium iodide (5.00 g, 30.1 mmol) in $H_2O$. The suspension was allowed to stand for 12 h, treated with $Et_2O$ (200 mL) and brine (200 mL), the layers separated, and the aqueous layer further extracted with fresh $Et_2O$ (2×300 mL). The combined organic portions were, filtered, washed with 1 N HCl (2×300 mL), brine (200 mL), dried ($K_2CO_3$), filtered, and concentrated in vacuo to afford 1.63 g (57%) of the product as a clear oil: $^1H$ NMR (300 MHz, $CDCl_3$) δ 3.23 (t, J=8 Hz, 2H), 4.63 (t, J=8 Hz, 2H), 6.75 (d, J=8 Hz, 1H), 7.02 (d, J=8 Hz, 1H), 7.29–7.42 (m, 5H).

Step 7

2,3-Dihydro-5-phenyl-4-benzofurancarboxylic acid: A magnetically stirred solution of 2,3-dihydro-4-iodo-5-phenylbenzofuran (1.60 g, 4.97 mmol) in anhydrous THF (40 mL) under nitrogen at −78° C. was treated with tert-butyllithium (1.73 M in pentane, 6.10 mL, 10.6 mmol), keeping the temperature less than −65° C., throughout. The solution was stirred for 0.5 h and treated with anhydrous carbon dioxide over 1 h at such a rate as to keep the temperature below −60° C. during addition. The solution was stirred for 2 h, allowed to warm to room temperature, and treated with $Et_2O$, ice (100 g), and 1 N NaOH (200 mL). The layers were separated and the organic portion was further extracted with fresh 1 N NaOH (2×200 mL). The combined organic extracts were acidified with concentrated HCl, extracted with $CH_2Cl_2$ (3×150 mL), and the extracts washed with brine (200 mL), dried ($MgSO_4$), filtered, and concentrated in vacuo to give 0.795 g (67%) of the title compound: $^1H$ NMR (300 MHz, $CDCl_3$)δ 3.45 (t, J=8.5 Hz, 2H), 4.65 (t, J=8.5 Hz, 2H), 6.93 (d, J=8 Hz, 1H), 7.14 (d, J=8 Hz, 1H), 7.29–7.42 (m, 5H), 11.2 (br s, 1H).

Preparation of intermediates of formula 5 where X=O and Z=$(CH_2)_n$.

Step 1

6-Bromo-2,3-dihydroxybenzaldehyde: 6-Bromo-2-hydroxy-3-methoxybenzaldehyde (2.00 g, 8.65 mmol) was dissolved in methylene chloride (10 mL) and cooled to 0° C. Boron tribromide (17.0 mL of a 1.0 M solution, 17.00 mmol) was added by syringe and the solution was stirred at 0° C. for 1 h before allowing the reaction to warm up to ambient temperature and stir for 15 h at which time TLC analysis indicated the reaction complete. The reaction mixture was poured onto ice and extracted with ethyl acetate. The organic layers were dried with magnesium sulfate and concentrated by rotary evaporation to afford 1.82 g of 6-bromo-2,3-dihydroxybenzaldehyde (8.39 mmol, 97% yield) as a yellow solid.

Step 2

5-Bromo-1,3-benzodioxole-4-carboxaldehyde: 6-Bromo-2,3-dihydroxybenzaldehyde (1.82 g, 8.39 mmol) was dissolved in DMF (20 mL) and dibromomethane (1.57 g, 9.00 mmol) and potassium fluoride (2.44 g, 42.00 mmol) were added. The reaction mixture was heated to 100° C. for 2 h at which time TLC analysis indicated the reaction complete. The reaction mixture was cooled to ambient temperature and partitioned between water and methylene chloride. The organic layers were washed 4× with water, dried with magnesium sulfate, and concentrated by rotary evaporation to afford 0.60 g of product (2.62 mmol, 31% yield) as an oil. $^1H$ NMR ($CDCl_3$) δ 10.24 (s, 1H), 7.09 (d, J=8.3 Hz, 1H), 6.79 (d, J=8.3 Hz, 1H), 6.10 (s, 2H).

Step 3

5-Bromo-1,3-benzodioxole-4-carboxylic acid: Potassium permanganate (1.03 g, 6.55 mmol) was dissolved in water (25 mL). 5-Bromo-1,3-benzodioxole-4-carboxaldehyde (0.60 g, 2.62 mmol) was dissolved in acetone (25 mL) and slowly added to the permanganate solution and the reaction mixture was stirred at ambient temperature for 24 h at which time TLC analysis indicated the reaction complete. The reaction mixture was quenched with 5% sodium sulfite (100 mL). Concentrated HCl (10 mL) was added and the mixture turned a pale yellow color. The solution was extracted with ethyl acetate and the organic layers were dried with magnesium sulfate and concentrated by rotary evaporation to afford 0.34 g of product (1.39 mmol, 53% yield) as an off-white solid.

Step 4

5-Bromo-1,3-benzodioxole-4-carboxylic acid, methyl ester: 5-Bromo-1,3-benzodioxole-4-carboxylic acid (0.34 g, 1.39 mmol) was dissolved in methanol (25 mL). A few drops of concentrated sulfuric acid were added and the solution was heated to reflux for 60 h at which time TLC analysis indicated the reaction complete. The reaction was cooled and poured into a solution of 5% $NaHCO_3$ (25 mL) and extracted with ethyl acetate. The organic layers were dried with magnesium sulfate and concentrated by rotary evaporation to afford 0.20 g of product (0.77 mmol, 55% yield) as an off-white solid. $^1H$ NMR ($CDCl_3$) δ 7.11 (d, J=8.3 Hz, 1H), 6.78 (d, J=8.3 Hz, 1H), 6.09 (s, 2H), 3.95 (s, 3H).

Step 5

5-(4-methoxyphenyl)-1,3-benzodioxole-4-carboxylic acid, methyl ester: 5-bromo-1,3-benzodioxole-4-carboxylic acid methyl ester. (0.20 g, 0.77 mmol), 4-methoxyphenylboronic acid (0.12 g, 0.77 mmol), and tris(dibenzylideneacetone) dipalladium (0) (7 mg) were added to dimethoxyethane (10 mL) and 2 M sodium carbonate (10 mL). The reaction was heated to reflux for 16 h at which time TLC analysis indicated the reaction complete. The reaction mixture was decanted and the residue extracted with ethyl acetate. The combined organic layers were dried and the solvent removed by rotary evaporation to afford the crude biphenyl ester.

Step 6

5-(4-Methoxyphenyl)-1,3-benzodioxole-4-carboxylic acid: The crude 5-(4-methoxyphenyl)-(1,3)-benzodioxole-4-carboxylic acid, methyl ester was hydrolyzed with 1 N sodium hydroxide (2 mL) in refluxing ethanol (10 mL) until TLC analysis indicated the completion of the reaction. The cooled reaction mixture was extracted with methylene chloride and then the aqueous layer was acidified with 1 N hydrochloric acid. The acidic solution was extracted with methylene chloride and the organic layers were dried and concentrated by rotary evaporation to give the crude acid. Preparation of intermediates of formula 7.

(2,10-Dihydro-1H-fluoreno[2,1-b]furan-10-ylidene) acetonitrile: A magnetically stirred solution of 2,3-dihydro-5-phenyl-4-benzofurancarboxylic acid (0.730 g, 3.04 mmol) in thionyl chloride (250 mL) was heated at reflux for 3 h. The solvent was removed by concentration in vacuo. The residue was digested with $CH_2Cl_2$ (150 mL) and the solution concentrated in vacuo. This process was repeated twice. The residue was digested with $CH_2Cl_2$ (260 mL) and treated with anhydrous aluminum chloride (0.40 g, 3.00 mmol). The resultant suspension was stirred for 2 h, poured over ice (250 g), treated with 1 N HCl (250 mL) and $CH_2Cl_2$ (250 mL), the layers were separated, and the aqueous layer further extracted with fresh $CH_2Cl_2$ (3×200 mL). The combined organic extracts were washed with brine (500 mL), dried ($K_2CO_3$), filtered, and concentrated in vacuo to give 0.525 g of 2,10-dihydro-1H-fluoreno[2,1-b]furan-10-one: $^1$H NMR (300 MHz, CDCl$_3$) δ 3.44 (t, J=8.5 Hz, 2H), 4.65 (t, J=8.5 Hz, 2H), 6.78 (d, J=8 Hz, 1H), 7.18 (dt, J=1.5, 8 Hz, 1H), 7.25 (d, J=8 Hz, 1H), 7.39 (d, J=8 Hz, 1H), 7.41 (dt, J=2, 8 Hz, 1H), 7.57(d, J=8 Hz, 1H).

A magnetically stirred solution of diethyl cyanomethylphosphonate (0.502 g, 2.83 mmol) in anhydrous THF (150 mL) was treated with sodium hydride (60% in mineral oil, 0.113 g, 2.82 mmol) in portions. The resultant suspension was treated dropwise with 2,10-dihydro-1H-fluoreno[2,1-b]furan-10-one (0.525 g, 2.36 mmol) in THF (100 mL), stirred 12 h, poured over ice (100 g), and treated with brine (100 mL), and Et$_2$O (150 mL). The layers were separated and the aqueous layer further extracted with fresh Et$_2$O (2×150 mL). The combined organic extracts were washed with brine (200 mL), dried ($K_2CO_3$), filtered, and concentrated in vacuo.

(8-Methoxy-10H-fluoreno[1,2-d]-1,3-dioxol-10-ylidene) acetonitrile: Crude 5-(4-methoxyphenyl)-1,3-benzodioxole-4-carboxylic acid was dissolved in thionyl chloride (10 mL) and refluxed for 6 h. The reaction was cooled to ambient temperature and the solvent was removed by rotary evaporation to give the crude acid chloride. The acid chloride was dissolved in methylene chloride (10 mL) and added to a suspension of aluminum chloride (0.67 g, 5.00 mmol) in methylene chloride (10 mL). The reaction was stirred at ambient temperature for 4 h and quenched with a mixture of ice and concentrated HCl. The mixture was extracted with methylene chloride and dried with magnesium sulfate and concentrated by rotary evaporation to afford 89 mg of 8-methoxy-10H-fluoreno[1,2-d]-1,3-dioxol-10-one (0.35 mmol, 45% yield). $^1$H NMR (300 MHz, CDCl$_3$) δ 7.54 (d, J=8.3 Hz, 1H), 7.10 (d, J=8.3 Hz, 1H), 7.06 (d, J=2.2, 1H), 6.88 (dd, J=8.3, 2.2 Hz, 1H), 6.90 (d, J=8.3 Hz, 1H), 6.15 (s, 2H), 3.86 (s, 3H). Sodium hydride (21 mg, 0.53 mmol) was suspended in THF (5 mL) and diethyl cyanomethylphosphonate (94 mg, 0.53 mmol) was slowly added to the suspension. After 15 min a yellow solution resulted and a solution of 8-methoxy-10H-fluoreno[1,2-d]-1,3-dioxol-10-one (89 mg, 0.35 mmol) in THF (5 mL) was added dropwise. The solution was allowed to stir at ambient for 16 h. The solvent was removed by rotary evaporation and the residue was taken up in methylene chloride, washed with water, and dried with magnesium sulfate. The solvent was removed by rotary evaporation to yield the crude Horner-Emmons product as an orange solid.

EXAMPLES

The following examples illustrate the preparation of the inventive compounds and their melatonergic properties.

Example 1

N-[2-(2,10-dihydro-1H-fluoreno[2,1-b]furan-10-yl) ethyl]propanamide

The (2,10-dihydro-1H-fluoreno[2,1-b]furan-10-ylidene) acetonitrile obtained from 0.525 g (2.36 mmol) of 2,10-dihydro-1H-fluoreno[2,1-]furan-10-one was added to a Parr bottle, treated with Raney Nickel (~0.5 g) and propionic anhydride (100 mL), and rocked under hydrogen (60 psi) for 12 h. The suspension was filtered through Celite and the Celite rinsed with $CH_2Cl_2$ (600 mL). The filtrate was concentrated in vacuo, and the residue was subjected to flash chromatography (silica gel, 1:2 hexane-EtOAc elution) to give, after drying, 311 mg of a white solid: mp 153–154.5 °C.; $^1$H NMR (300 MHz, CDCl$_3$) δ 0.90 (t, J=7.6 Hz, 3H), 1.81 (q, J=7.6 Hz, 2H), 2.31–2.42 (m, 1H), 2.46–2.57 (m, 1H), 2.79–2.97 (m, 2H), 3.19–3.30 (m, 1H), 3.38–3.49 (m, 1H), 4,11 (br t, J=4.3 Hz, 1H), 4.58–4.72 (m, 3H), 6.82 (d, J=8.1 Hz, 1H), 7.25 (dt, J=1.1, 7.4 Hz, 1H), 7.34 (t, J=7.0 Hz, 1H), 7.46 (d, J=7.5 Hz, 1H), 7.52 (d, J=8.1 Hz, 1H), 7.65 (d, J=7.5 Hz, 1H); IR (NaCl Film) 3294, 1641, 1547, 1453, 1235, 983, 818, 762, 739 cm$^{-1}$; MS (ESI) m/e 259 (M-H–); Analysis calc'd for $C_{20}H_{21}NO_2$ 0.20 ($H_2O$): C, 77.24; H, 6.94; N, 4.50; found: C, 77.31, H, 6.70; N, 4.11.

Example 2

N-[2-(8-Methoxy-10H-fluoreno[1,2-d]-1,3-dioxol-10-yl)ethyl]propanamide

The crude (8-methoxy-10H-fluoreno[1,2-d]-1,3-dioxol-10-ylidene)acetonitrile obtained from 89 mg (0.35 mmol) of 8-methoxy- 10H-fluoreno[1,2-d]-1,3-dioxol-10-one was dissolved in EtOH (10 mL) and CHCl$_3$ (3 mL) and hydrogenated in a Parr shaker at 50 psi with platinum oxide for 18 h. The suspension was filtered and the solvents removed by rotary evaporation to yield crude 2-(8-methoxy-10H-fluoreno[1,2-d]-1,3-dioxol-10-yl)ethyl amine hydrochloride. The amine hydrochloride was suspended in methylene chloride (10 mL) with triethylamine (0.10 g, 1.00 mmol) and a catalytic amount of 4-dimethylaminopyridine (5 mg). A solution of propionic anhydride (69 mg, 0.53 mmol) in methylene chloride (2 mL) was slowly added to the amine solution and the resulting reaction was stirred at ambient temperature for 2 h. The reaction was quenched with 1N HCl and the layers separated. The aqueous layer was washed with methylene chloride and the combined organic layers were dried. The solvents were removed by rotary evaporation to afford the crude amide. Flash chromatography (25% ethyl acetate/hexane) afforded 26 mg of N-[2-(8-methoxy-10H-fluoreno[1,2-d]-1,3-dioxol-10-yl)ethyl]propanamide as a white solid, mp 145–147° C. $^1$H NMR (CDCl$_3$) δ 7.55 (d, J=8.3 Hz, 1H), 7.11 (d, J=8.3 Hz, 1H), 7.04 (d, J=2.2, 1H), 6.90 (dd, J=8.3, 2.2 Hz, 1H), 6.86 (d, J=8.3 Hz, 1H), 6.17 (s, 2H), 4.01 (t, J=5.2 Hz, 1H), 3.86 (s, 3H 3.07 (q, J=6.2 Hz, 2H), 2.32 (q, J=5.2 Hz, 2H), 1.89 (q, J=7.6 Hz, 2H), 0.96 (t, J=7.6 Hz, 3H). Anal. Calcd for C$_{20}$H$_{21}$N$_1$O$_4$: C, 70.78; H, 6.24; N, 4.13. Found: C, 70.68; H, 6.34, N, 4.12.

Melatonergic Binding Activity

Example 3

The melatonergic binding properties of compounds of the invention were measured using the following procedure.
1. Reagents
   (a) TME=50 mM Tris buffer containing 12.5 mM MgCl$_2$, and 2 mM EDTA, pH 7.4 at 37° C. with concentrated HCl.
   (b) Wash buffer: 20 mM Tris base containing 2 mM MgCl$_2$. pH 7.4 at room temperature.
   (c) 10$^{-4}$M melatonin (10$^{-5}$M final concentration).
   (d) 2-[$^{125}$I]-iodomelatonin, 0.1M final concentration.
2. Membrane Homogenates The melatonin ML$_{1A}$ receptor cDNA was subcloned into pcDNA3 and introduced into NIH-3T3 cells using Lipofectamine. Transformed NIH-3T3 cells resistant to geneticin (G-418) were isolated, and single colonies expressing high levels of 2[$^{125}$Iiodomelatonin binding were isolated. Cells were maintained in DMEM supplemented with 10% calf serum and G-418 (0.5 g/liter). Cells were grown to confluency in T-175 flasks, scraped using Hank's balanced salt solution, and frozen at –80° C. For preparing membrane homogenates, pellets were thawed on ice, and resuspended in TME buffer in the presence of 10 μg/ml aprotinin and leupeptin, and 100 μM phenylmethyl-sulfonylfluoride. The cells were then homogenized using a dounce homogenizer, and centrifuged. The resulting pellet was resuspended with dounce homogenizer in TME (supplemented with the above protease inhibitors) and frozen. On the day of assay, the small aliquot was thawed on ice and resuspended in ice cold TME (1:50–1:100 v/v) and held on ice until assayed.
3. Incubation: 37° C. for 1 hour. Reaction is terminated by filtration. Filters are washed 3 times.
4. References: Reppert, S. M., and Ebisawa, R. (1994). Neuron, 13, 1177–1185.

The compounds of Examples 1 and 2 have binding affinities for melatonin receptors with IC$_{50}$ values of less than 25 nM.

Reasonable variations, such as those which would occur to a skilled artisan, can be made herein without departing from the scope of the invention.

We claim:

1. A compound of Formula I or a pharmaceutically acceptable solvate thereof, Formula I being:

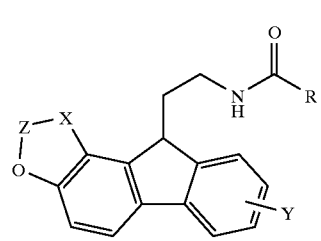

(I)

wherein

Z=CH (when a double bond is present) or (CH$_2$)$_n$, wherein n is 1–4;

X=O, CH$_2$, or CH (when a double bond is present);

R=C$_{1-6}$ alkyl, C$_{3-6}$ cycloalkyl, or C$_{1-3}$ haloalkyl, C$_{2-6}$ alkenyl, C$_{2-4}$ alkoxyalkyl, C$_{1-4}$ trifluoromethylalkyl, C$_{1-6}$ aminoalkyl; and Y=H, C$_{1-6}$ alkoxy or halogen.

2. The compound of claim 1 wherein Y is H and Z is CH$_2$.

3. The compound of claim 2 wherein X is CH$_2$.

4. The compound of claim 3 wherein R is C$_{1-6}$ alkyl.

5. The compound of claim 4, N-[2-(2,10-dihydro-1H-fluoreno[2,1-b]furan-10-yl)ethyl]propanamide.

6. The compound of claim 1 wherein Y is OCH$_3$ and Z is CH$_2$.

7. The compound of claim 6 wherein X is O.

8. The compound of claim 7 wherein R is C$_{1-6}$ alkyl.

9. The compound of claim 8, N-[2-(8-Methoxy-10H-fluoreno[1,2-d]-1,3-dioxol-10-yl)ethyl]propanamide.

10. A method of treating a sleep disorder in a patient in need of treatment comprising administering to said patient a therapeutically effective amount of a compound of claim 1.

11. A composition useful for treating a sleep disorder comprising a therapeutically effective amount of a compound of claim 1 and a pharmaceutically acceptable carrier.

12. A method of treating circadian rhythm disorder in a patient in need of treatment comprising administering to said patient a therapeutically effective amount of a compound of claim 1.

13. A composition useful for treating a circadian rhythm disorder comprising a therapeutically effective amount of a compound of claim 1 and of a pharmaceutically acceptable carrier.

* * * * *